United States Patent [19]

Newingham et al.

[11] 4,180,466
[45] * Dec. 25, 1979

[54] METHOD OF LUBRICATION OF A CONTROLLED-SLIP DIFFERENTIAL

[75] Inventors: Thomas D. Newingham, Broomall; Alexander D. Recchuite, Boothwyn, both of Pa.; John Q. Griffith, III, Claymont, Del.; Marcus W. Haseltine, Jr., Brookhaven, Pa.

[73] Assignee: Sun Ventures, Inc., St. Davids, Pa.

[*] Notice: The portion of the term of this patent subsequent to Jul. 23, 1991, has been disclaimed.

[21] Appl. No.: 489,216

[22] Filed: Jul. 17, 1974

Related U.S. Application Data

[63] Continuation-in-part of Ser. No. 116,985, Feb. 19, 1971, Pat. No. 3,825,495.

[51] Int. Cl.$^2$ .................. C10M 1/38; C07G 17/00
[52] U.S. Cl. ........................... 252/48.6; 260/125; 260/139
[58] Field of Search ............... 252/48.6; 260/125, 139

[56] References Cited
U.S. PATENT DOCUMENTS 3,825,495  7/1974  Newingham et al. ............ 252/48.6

Primary Examiner—Irving Vaughn
Attorney, Agent, or Firm—J. Edward Hess; Donald R. Johnson; Paul Lipsitz

[57] ABSTRACT

An improved method of lubrication of a controlled-slip differential comprises using a lubricant comprising major amounts of a hydrocarbon base stock and friction improving amounts of synthetic sulfurized oil consisting essentially of a cosulfurized blend of a triglyceride and a $C_2$–$C_{128}$ monoolefin. The hydrocarbon base stock can have a kinematic viscosity at 210° F. in the range of 1.5 to 200.0 cs. and contain paraffinic (by VGC) petroleum oil or a blend of at least one $C_{13}$–$C_{29}$ naphthene and from 0.1 to 20 parts by weight, based on said naphthene of at least one member from at least one of the following groups (a), (b), (c) and (d):

(a) a synthetic liquid $C_3$–$C_8$ olefin homopolymer, copolymer or terpolymer;
(b) a member from group (a) above which is at least partially hydrogenated;
(c) a severely hydrorefined naphthenic mineral oil lube containing less than 1 percent of gel aromatic hydrocarbons; and
(d) a severely hydrorefined paraffinic mineral oil lube containing less than 1 percent of gel aromatic hydrocarbons.

5 Claims, 4 Drawing Figures

CONTROLLED-SLIP DIFFERENTIAL

"GENERAL MOTORS R-H" FRICTION TESTER DATA

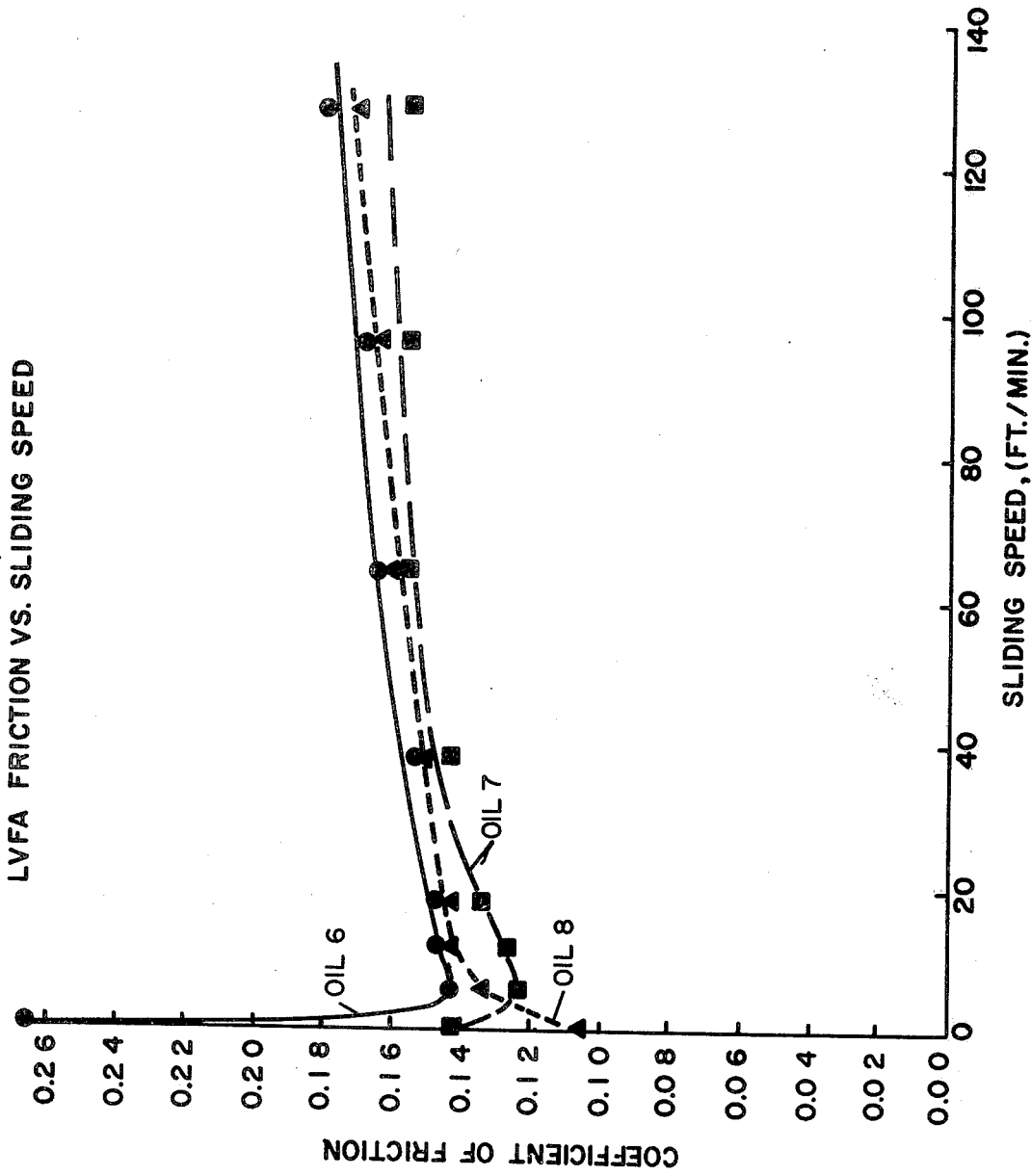

METHOD OF LUBRICATION OF A CONTROLLED-SLIP DIFFERENTIAL

CROSS REFERENCES TO RELATED APPLICATIONS

This application is a continuation-in-part of our application Ser. No. 116,985 filed Feb. 19, 1971, which issued July 23, 1974 as U.S. Pat. No. 3,825,495.

The present application is related to the following applications:

| SERIAL NO. (Patent No) | FILING DATE (Issue Date) | TITLE/INVENTOR(S) |
| --- | --- | --- |
| 679,834 (3,595,797) | 11-1-67 (7-27-71) | Blending Branched Paraffin Fluids for Use in Traction Drive Transmission - IRL N. DULING, DAVID S. GATES and MARCUS W. HASELTINE, JR. |
| 679,851 (3,598,740) | 11-1-67 (8-10-71) | Traction Drive Transmission Containing Paraffinic Oil as Lubricant - IRL N. DULING, DAVID S. GATES AND MARCUS W. HASELTINE, JR. |
| 812,516 (3,619,414) | 2-19-69 (11-9-71) | Catalytic Hydrofinishing of Petroleum Distillates in the Lubricating Oil Boiling Range - IVOR W. MILLS, MERRITT C. KIRK, JR. and ALBERT T. OLENZAK |
| 116,841 (3,843,534) | 2-19-71 | Lubrication of Controlled-Slip Differential - DAVIS D. GATES, PAUL E. HAGSTROM and MARCUS W. HASELTINE, JR. |
| 135,466 (abandoned) | 4-19-71 | Process of Sulfurizing Lard Oil and an Olefin and Resultant Product - ALEXANDER D. RECCHUITE |
| 218,394 (3,903,001) | 1-17-72 | Lubricant for a Controlled-Slip Differential - MARCUS W. HASELTINE, JR. DAVID S. GATES and PAUL E. HAGSTROM |
| 220,399 (pending) | 1-24-72 | Process of Sulfurizing Lard Oil and an Olefin and Resultant Product - ALEXANDER D. RECCHUITE |
| 298,126 (3,915,873) | 10-16-72 | Composition Comprising Naphthenic Distillate, Hydrocracked, Lube and an Antioxidant - ROBERT P. BRYER, THOMAS D. NEWINGHAM, IVOR W. MILLS and GLENN R. DIMELER |
| 397,473 (pending) | 9-14-73 | Oil Containing a Cosulfurized Olefin-Triglyceride Blend - ALEXANDER D. RECCHUITE |

The disclosure of Ser. No. 116,985 and of all of the above-cited applications is hereby incorporated herein (by this reference). In particular, these applications disclose blended lubricants which are useful in the present invention, additives which can be useful in such lubricants and processes for making individual components of such blends.

BACKGROUND OF THE INVENTION

As has been reported by R. L. Kostelak in *Lubrication*, Volume 56, #4, 1970 (pg 49 et seq.), the principle of operation of the conventional differential in today's American automobile remains the same as the Pecqueur differential, invented in 1827. Although this "conventional differential" generally performs very satisfactorily, it has one serious shortcoming; namely, "stalling," which occurs when either rear wheel loses traction. Due to the kinematics of the conventional differential design, the driving torque is divided equally between the two rear wheels and is limited by the wheel with the least traction. Hence, when one wheel loses traction, the vehicle does not move.

To prevent this shortcoming, engineers have developed many ingenious ideas and mechanisms. Each manufacturer has his own descriptive name for his particular mechanism; for example, Chevrolet Positraction, Chrysler Sure-Grip, and Ford Traction-Lok. Generally, however, a differential incorporating one of these mechanisms is called a "locking" or "limited slip" or "controlled-slip" differential.

The limited slip differential used in the American passenger car is essentially the same as a conventional differential except for the incorporation of some form of friction members (e.g., clutch plates or friction cones). The Kostelak article describes the conventional differential and typical controlled-slip differentials. Another pertinent article is "Lubricants for Limited Slip Differentials" by John W. Allen, given at Fuels and Lubricants Meeting, Society of Automotive Engineers, Houston, Tex., Nov. 1–3, 1966.

U.S. Pat. No. 3,211,653 of O'Halloran discusses the problems of lubrication of a limited slip differential and reports that the addition of sulfurized sperm oil to such a lubricant produces severe noise on "sharp turn with braking." We have discovered that, contrary to the O'Halloran teachings, a cosulfurized blend of a triglyceride and a $C_2$–$C_{128}$ monoolefin can be useful in lubrication of a limited slip differential.

SUMMARY OF THE INVENTION

An improved method of lubrication of a controlled-slip differential comprises using a lubricant comprising major amounts of a hydrocarbon base stock and friction improving amounts of synthetic sulfurized oil consisting essentially of a cosulfurized blend of a triglyceride and a $C_2$–$C_{128}$ monoolefin. The hydrocarbon base stock can have a kinematic viscosity at 210° F. in the range of 1.5 to 200.0 cs. and contain paraffinic (by VGC) petroleum oil or a blend of at least one $C_{13}$–$C_{29}$ naphthene and from 0.1 to 20 parts by weight, based on said naphthene of at least one member from at least one of the following groups (a), (b), (c) and (d):

(a) a synthetic liquid $C_3$–$C_8$ olefin homopolymer, copolymer or terpolymer;

(b) a member from group (a) above which is at least partially hydrogenated;

(c) a severely hydrorefined naphthenic mineral oil lube containing less than 1 percent of gel aromatic hydrocarbons; and (d) a severely hydrorefined paraffinic mineral oil lube containing less than 1 percent of gel aromatic hydrocarbons.

Preferably, the amount of said blend which is present in said base stock is sufficient to provide a greater coefficient of traction, measured at 600 feet per minute, 200° F., 400,000 psi, than would be provided by substitution of the same amount of ASTM Oil No. 3 for said blend in said base stock. Typically, the lubricant contains 0.5 to 10 volumes of synthetic sulfurized oil for each 100 volumes of said base stock. The paraffinic oil can be a bright stock, or a raffinate from solvent extraction, and can have been hydrorefined or hydrocracked. A useful species of the paraffinic petroleum oil base stock has a viscosity-gravity constant no greater than 0.819.

In one embodiment a combination of a controlled-slip differential and a lubricant therefor, we have discovered an improvement wherein said lubricant comprises (A) synthetic sulfurized oil comprising a sulfurized blend of lard oil and a $C_{12}$–$C_{14}$ monoolefin and (B) a hydrocarbon base stock having a kinematic viscosity at 210° F. in the range of 1.5 to 200.0 cs., said base stock containing a blend of at least one $C_{13}$–$C_{29}$ naphthene and from 0.1 to 20 parts by weight, based on said naphthene, of at least one member from at least one of the following groups (a), (b), (c) and (d):

(a) a synthetic liquid $C_3$–$C_8$ olefin homopolymer, copolymer or terpolymer;

(b) a member from group (a) above which is at least partially hydrogenated (preferably, to an iodine number less than 20, more preferably less than 5 and/or having a 195 UVA less than 2.0);

(c) a severely hydrorefined naphthenic lube containing less than 1 percent of gel aromatic hydrocarbons;

(d) a severely hydrorefined paraffinic lube containing less than 1 percent of gel aromatic hydrocarbons;

and wherein the amount of said blend which is present in said base stock is sufficient to provide a greater coefficient of traction, measured at 600 feet per minute, 200° F., 400,000 psi, than would be provided by substitution of the same amount of ASTM Oil No. 3 for said blend in said base stock. The preferred lubricant has a viscosity in the range of 5 to 50 cs. at 210° F., has a channel point below 32° F. (more preferred below 10° F., typically 0° to −25° F.) and also contains an extreme pressure (EP) additive (e.g., tricresyl phosphate, zinc dithiophosphate, etc.) and an additive which lowers the static friction of the lubricant, one such static friction modifier is a surface-active, organic phosphate ester of a linear aliphatic, ethoxylated alcohol. The molecular weight and degree of ethoxylation are chosen so that the ester has sufficient solubility in the base stock to provide the desired degree of reduction of static friction.

Preferably, the $C_{13}$–$C_{29}$ naphthene has a glass transition temperature in the range of −90° to −30° C. and contains as a structural nucleus, a cyclohexyl hydrindan, di(cyclohexyl)alkane, adamantane, spriodecane, spiropentane, perhydrofluorene, perhydrobiphenyl, perhydroterphenyl, decalin, norbornane, perhydroindacene, perhydrohomotetraphthene, perhydroacenaphthene, perhydrophenanthrene, perhydrocrysene, perhydroindane-1-spirocyclohexane, perhydrocarylophyllene, pinane, camphane, perhydrophenylnaphthalene or perhydropyrene.

These blended hydrocarbon base stocks are described in the aforementioned applications of Duling et al. ASTM Oil No. 3 is described, for example, in U.S. Pat. No. 3,598,740. Naphthenic and paraffinic oils are described, for example, in Bruins, P. F., *Plasticizer Technology*, pages 79, 80 and 85, Volume 1, Reinhold Pub., New York, 1965.

In general, the lubrication of a limited slip differential can be improved by use of a lubricant composition comprising a major portion of a mineral oil and a minor portion of a cosulfurized blend of from 50 to 90 parts by volume of a triglyceride wherein the fatty acid moieties of said triglyceride contain principally from 9 to 22 carbon atoms and at least about 45 mole percent of the fatty acid moieties present contain an ethylenically unsaturated carbon-carbon double bond and wherein said fatty acid moieties are hydrocarbons except for the carboxylic group of said fatty acid moieties, and from 50 to 10 parts by volume of a hydrocarbon containing from 2 to about 128 carbon atoms and having the structure:

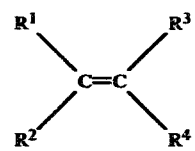

wherein $R^1$, $R^2$ and $R^3$ are either hydrogen or alkyl and $R^4$ is either hydrogen, alkyl, aryl, cycloalkyl, or alkaryl, which cosulfurized blend contains chemically combined therewith from 7.5 to 25 weight percent as based on said blend of sulfur.

In one embodiment $R^4$ is alkyl and, preferably, $R^2$ and $R^3$ are hydrogen. More preferred, $R^1$ is hydrogen. A preferred glyceride is lard oil. Such cosulfurized blends are further described in Ser. No. 397,473 of Recchuite and Ser. No. 218,394 of Haseltine et al.

Figure 1:
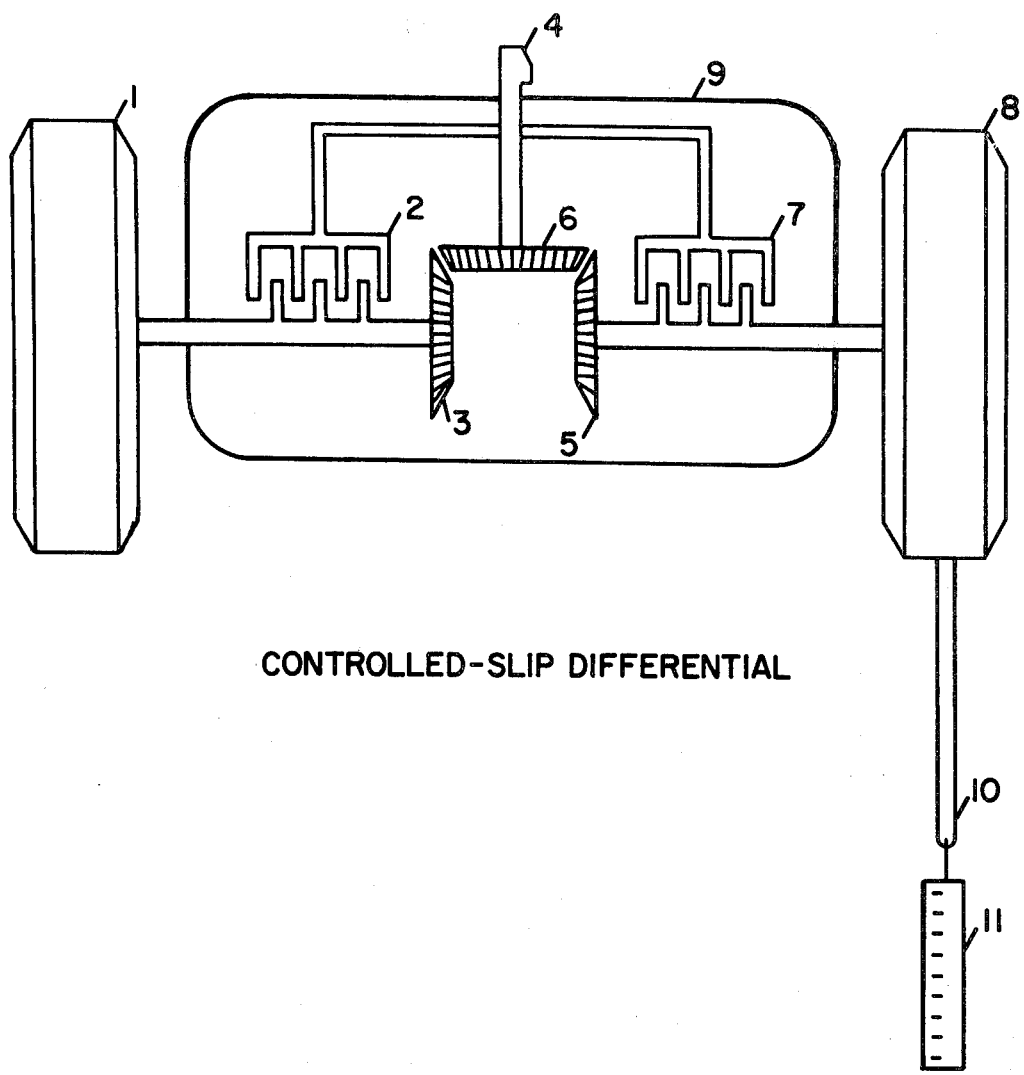
FIG. 1 of the accompanying drawings is an illustration of a controlled-slip differential and will be referred to with reference to a test method for comparing the dynamic torque obtained from a given combination of lubricant and controlled-slip differential. The test can be useful in comparing various lubricants in a given differential.

For example, in a limited slip differential (LSD), the contact plates can be surfaced with swirl patterns to produce high friction. When the plate has become worn, the friction drops drastically and the LSD fails to perform any better than a conventional differential. With a high traction-LSD fluid, the friction property is inherent in the fluid itself and is not completely dependent on the patterned contact surfaces. Thus, the lubricated contacts can have high friction (or traction) even when badly worn.

With reference to the figure, torque measurements are made by attaching a belt (10) around one of the rear wheels (8) and connecting the belt end to a calibrated spring scale (11). The other rear wheel (1) is then turned by hand to slip the differential. The measurement when slip begins is taken as the "break-free torque." A second measurement is determined at approximately 40 rpm (with the wheel (1) being driven by a motor).

The differential in the figure consists of a ring gear (4), a differential pinion (6) and cross shaft, and a right (7) and a left (2) clutch plate attached to the differential case. The wheels are connected to the differential pinion by the right (5) and left (3) side gears. Clutch plates are also attached to the left and right axle shafts. The differential assembly and the lubricant are contained in a housing (9).

Figure 2:
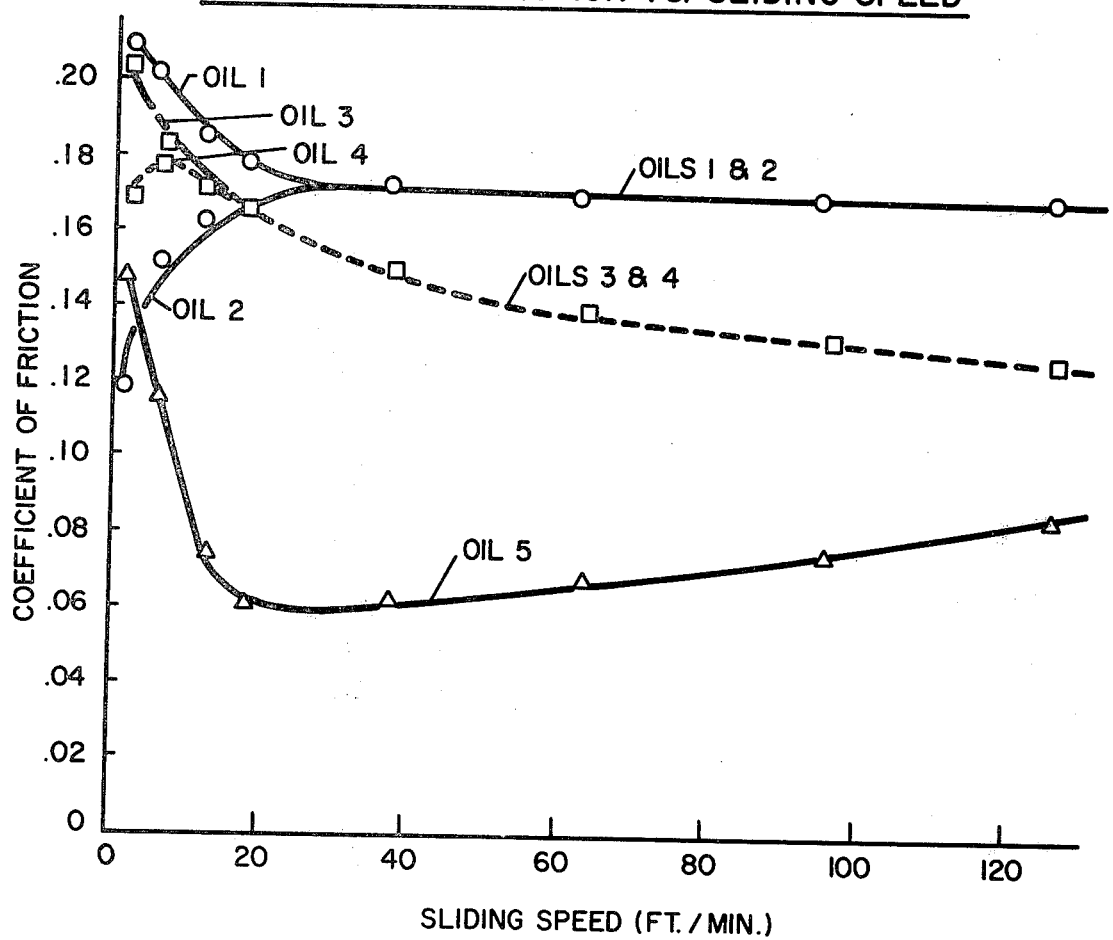
Figure 3:
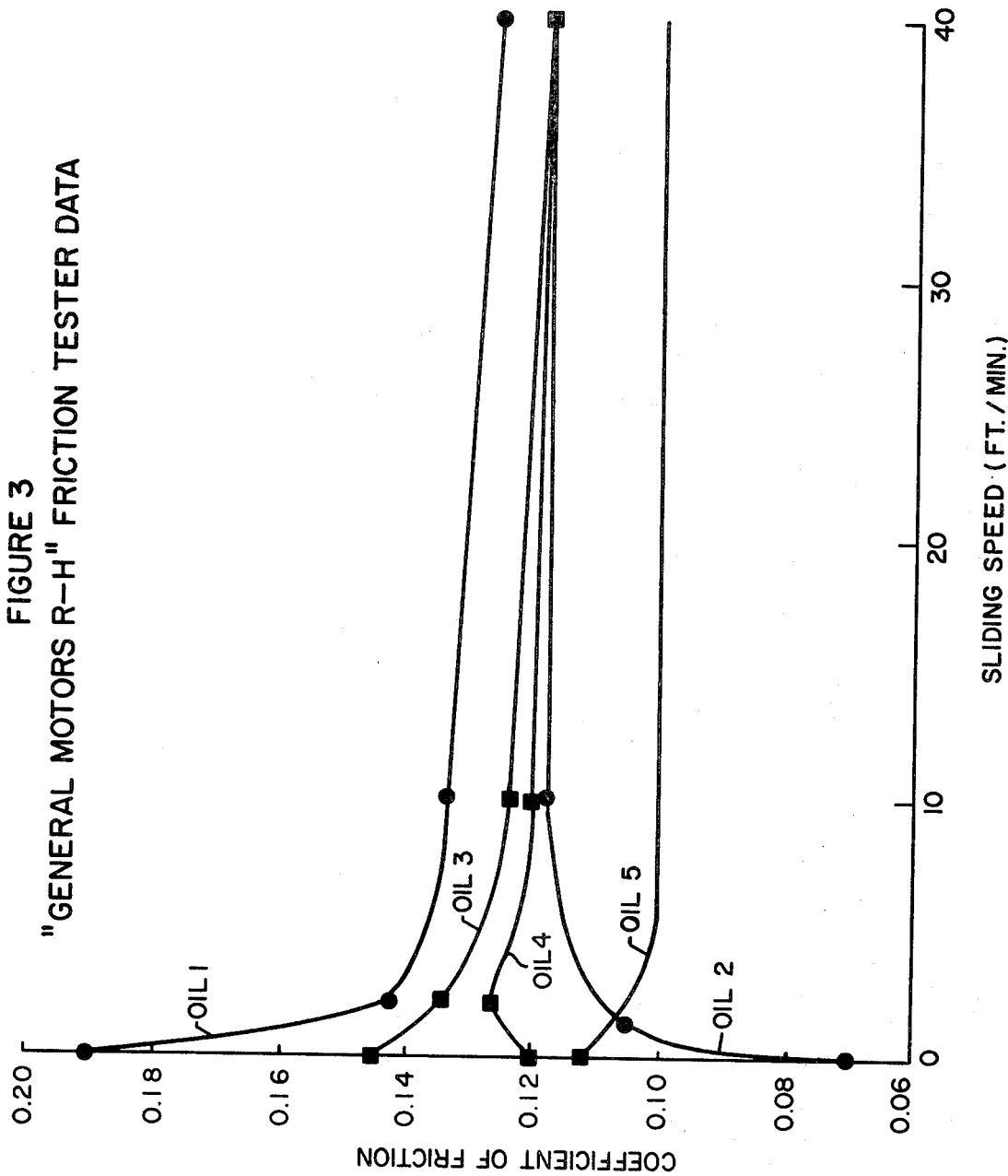

FIGS. 2, 3 and 4 illustrate, for a number of lubricants, the relationship between the static coefficient of friction and the dynamic coefficient of friction at various sliding speeds. The FIGS. 2 and 4 data were obtained by the "LVFA" method; whereas, the FIG. 3 data was obtained by the "R-H" method.

FURTHER DESCRIPTION

The synthetic, cosulfurized oil can, for example, be obtained by sulfurizing a blend of 90 to 30 parts by weight of lard oil (or other triglyceride) and 10 to 70 parts of an olefin containing 2 to 128 (preferably, 12 to 24) carbon atoms. The sulfurization can be carried out using elemental sulfur, especially for oils containing 6 to 11 percent sulfur. Sulfur monochloride can be used for both sulfurizing and chlorinating simultaneously. The sulfurization involves cooking at from 330° to 445° F. for 20 minutes to 10 hours followed by blowing with a gas (preferably, at from 125° to 340° F. for 30 minutes to 20 hours) to remove hydrogen sulfide. With sulfur monochloride, the preferred cooking temperature is in the range of 150 to 250 (under pressure if desired). Small amounts of water can act as a promoter for the reaction. The sulfurized oils can contain from 5 to 25 weight percent sulfur as based on the blend of olefin and lard oil (i.e., 5 to 25 parts by weight of sulfur per 100 parts by weight of olefin-lard oil blend).

For example, one embodiment of the invention involves using the previously described lubricants and from 0.1 to 10 percent of a composition consisting essentially of a sulfur-containing chemical reaction product of a mixture of lard oil and a "true" isobutylene oligomer (e.g., see Ser. No. 218,394).

The amount of sulfur in a given sample of the cosulfurized oil is readily determined by X-ray fluorescene. After the amount of total sulfur is determined, 100 grams of the oil sample and 20 grams of copper powder are placed in a tall 250 milliliter beaker set up on a hot plate and equipped with a thermometer and an Unger stirrer operated at 1750 rpm. The sample is heated to 350° F. within a 5 minute period and maintained at 350°±5° F. for one hour after which it is cooled and filtered through filter paper to remove the copper powder. The sulfur content of the sample is again determined by X-ray fluorescence, and reported as inactive sulfur. The loss of sulfur (total minus inactive sulfur) is the amount of active sulfur in the original. The amount of active sulfur in the sulfurized oil being used as a friction modifier should be less than 2.5 percent. Generally, the preferred friction modifiers which contain 6 to 11 percent total sulfur will also contain from 1 to 2 percent active sulfur.

The preferred lard oil is winter grade.

After cooking the sulfurized oil is blown with a gas to remove $H_2S$. Any gas may be used which dissolves (or otherwise removes) $H_2S$ and does not significantly react with the sulfurized oil. Suitable gases include air, nitrogen, carbon dioxide and gaseous perhalogenated hydrocarbons. Air is preferred for obvious economic considerations. The blowing is most simply carried out by bubbling the gas through the sulfurized oil. Alternatively, the oil may be sprayed into the gas or a falling curtain of the oil in the gas may be used. Generally, the blowing is carried out at from 125° to 340° F. In the case of the sulfurized oils containing minimal active sulfur, the blowing should not be carried out above about 250° F. when air is the gas. When a high sulfur content (16 to 30 percent) oil is being made, it is preferred to use gas blowing temperatures above 190° F., as this minimizes the active sulfur lost in processing.

The sulfurized oils described above are useful as friction modifiers in fluids of the present invention to reduce the static friction more than the dynamic friction. Generally, in such fluids the sulfurized oils are used at from 0.5 to 10 percent, typically 1 to 5 percent, of the over-all fluid.

One important property of an LSD lubricant is the relationship between the static coefficient of friction and the dynamic coefficients of friction at various sliding speeds. Generally, the required coefficients are for steel on steel; however, other reference materials can be used (e.g., steel on paper) depending on the mechanism to be lubricated.

The preferred methods for obtaining the required friction coefficients include two.

One is the "LVFA" (or Low Velocity Friction Apparatus) method. The LVFA method is described by T. D. Newingham in Publication 774A of the Society of Automotive Engineering (National Fluids and Lubricants Meeting, Tulsa, Okla., Oct. 30 and 31, 1963).

The second method is the "R-H" method, which is described by M. L. Haviland et al., "Friction Characteristics of Controlled-Slip Differential Lubricants", pages 828 to 843, S.A.E. Transactions (1967).

Certain of the lubricants of the present invention, as will be further described hereinafter, produce unusual and very desirable friction curves when measured by either of these methods. These desirable curves can be described as "low static-high dynamic friction." In addition to the synthetic sulfurized oil, an important component of these desirable lubricants is an effective amount of a surface-active organic phosphate ester of a linear aliphatic, ethoxylated alcohol, said amount (e.g., 0.1 to 10 weight percent) being effective to reduce the static friction while not greatly reducing the dynamic friction. The molecular weight and degree of ethoxylation are chosen so as to attain the desired degree of oil solubility. In general, the sulfurized oil is present at from 0.5 to 10 weight percent, typically 1 to 5 percent, of the final lubricant.

ILLUSTRATIVE EXAMPLES

Example 1

466 grams of a commercial alpha-methyl styrene polymer, obtained by conventional acid-catalyzed polymerization, is placed in a one liter round-bottomed flask, attached to a one-inch column, and dry-distilled with essentially no reflux or fractionation at a pot temperature of about 290° C., and a vapor temperature of about 210° C. under a vacuum of about six millimeters of mercury. 373 grams of distillate are obtained and about 73 grams of material remain in the bottom of the flask at the end of the distillation. The commercial alpha-methyl styrene polymer has a softening point of 210° F., a Gardner-Holdt viscosity of J-L, a specific gravity of 1.075, a refractive index at 20° C. of 1.61, a molecular weight of 685, an iodine number of 0, an acid number of 0, and a saponification number of 0.

Example 2

300 grams of the distillation product of Example 1 are placed in a 316 stainless steel bomb along with 7.5 grams of Raney nickel catalyst and the bomb is pressured to 3000 psig of 100 percent hydrogen while heat is applied until the temperature in the bomb is 150° C. At that point an exothermic reaction occurs and heating is discontinued. The temperature is allowed to rise to about 220° C. and the hydrogen pressure is maintained at 3000 psi for 6 hours, at which time the bomb is slowly cooled to ambient temperature while maintaining the hydrogen pressure at 3000 psi in order to avoid dehydrogenation of the hydrogenated product. The resulting perhydrogenated poly(alpha-methyl styrene) oil is topped to remove components boiling below 125° C. The remaining perhydrogenated naphthene product has a KV210 of 11.07 cs. and a KV100° F. of 327.8 cs. Analysis by nuclear magnetic resonance (NMR) shows the oil of this example to contain about 40 percent of trimers (mostly hydrindan form), and 60 percent dimers, mainly, 1,1,3-trimethyl-3-cyclohexyl hydrindan.

Example 3

A blend of two commercially available polybutene polymers (i.e., 90 volume percent Indapol L-100 and 10 percent Oronite Special 6) is completely hydrogenated to produce a hydrogenated polybutene oil which analyzes 0.5 mole percent olefin by the ultraviolet absorbence method. The hydrogenation is at 200° C., 2000 psi of 100 percent hydrogen for 6 hours using Harshaw N10104P catalyst. The resulting hydrogenated polyolefin oil has a KV210° C. of 13.54 cs. and a KV100 of 162.8.

Example 4

A blended base oil was compounded from 61.0 volumes of the naphthene product of Example 2 and 33.1 volumes of the hydrogenated polyolefin oil of Example 3. Then 5.9 volumes of a commercial "limited slip axle additive" (Lubrizol Company, Anglamol 99LS) was added to the blend to produce a formulated lubricant. Table I describes typical properties of Anglamol 99LS.

TABLE I

| Specific Gravity at 60° F. (15.6° C.) | 1.055 |
|---|---|
| Pounds per Gallon at 60° F., U. S. | 8.79 |
| Pounds per Gallon at 60° F., IMP. | 10.55 |
| Viscosity at 210° F. (98.9° C.), SUS | 60 |
| Viscosity at 210° F., cSt. | 10.2 |

| Weight percent of: | Typical |
|---|---|
| Sulfur | 29.2 |
| Phosphorus | 2.0 |

The addition of an oil soluble, cosulfurized blend of a triglyceride and a $C_2$–$C_{128}$ olefin to this lubricant can improve antiwear and/or lower static friction.

Similarly, other blended base oils (e.g., comprising synthetic paraffins and naphthenes) and other gear oil additives can be used to formulate such lubricants. Other useful additives are those mentioned by F. G. Rounds, *Journal of Chemical and Engineering Data*, Volume 5, No. 4, October 1970, pages 504 and 505, and in application Ser. No. 218,394.

Example 5

Another useful lubricant for a controlled-slip differential, and which is also useful for lubrication of a traction drive transmission, comprises a blend of the following (all hydrogenations are to at least 98 percent saturation):

| Volume % | Component | KV210° F. (cs.) | KV100° F. (cs.) |
|---|---|---|---|
| 7.0 | Hydrogenated Cosden SH06 Polybutene | 11.04 | 124 |
| 28.0 | Hydrogenated Cosden SH15 Polybutene | 33.5 | 744 |
| 31.6 | Hydrogenated Poly Alpha-Methyl Styrene | 23 | 2463 |
| 21.0 | Hydrogenated Poly Alpha-Methyl Styrene | 4.65 | 39.6 |
| 7.4 | Anglamol 93 (EP Additive) | | |
| 3.0 | Amoco 9000 (Dispersant) | | |
| 1.0 | Ultraphos 11, (Low Static Modifer) | | |
| 1.0 | Synthetic Sulfurized Oil | | |

The use in this lubricant of high and low viscosity fractions of the naphthene and paraffin is an example of "dumbell-blending" to improve viscosity index.

The Ultraphos 11 additive is a surface-active, organic phosphate ester of a linear aliphatic ethoxylated alcohol.

The synthetic sulfurized oil is described in the previously cited applications of Alexander D. Recchuite. This oil can be used as a replacement for sulfurized sperm oil and can be made, for example, by heating sulfur and a blend of from 50 to 95 percent lard oil and 50 to 5 percent of one or a mixture of $C_{12}$–$C_{24}$ acyclic monoolefin. For example, 10 weight percent of sulfur was added at 250° F. to 90 weight percent of a blend of 85 volumes of lard oil (extra winter strained) and 15 volumes Chevron $C_{15}$–$C_{20}$ alpha-olefin. The sulfur-containing mixture was heated to 375° F. and maintained at that temperature with stirring, for two hours, then cooled to 200° F., and finally, blown with air for one hour.

Another procedure for making the synthetic sulfurized oil is to heat the lard oil-olefin blend to about 300° F., add sulfur (e.g., 5 to 25 percent) over a 30 minute period (with agitation), then bring the temperature to 335° F., maintain for one-half hour (also with agitation), cool to 200° F., and blow with air (at 200° F.) for 16 hours.

The channel point of a lubricant is determined by drawing a channel with a spatula in a sample of lubricant, at a given temperature, and finding the maximum temperature where the walls of the channel no longer cave-in.

Any of the usual gear lube additives can be used in the lubricant-differential combination of the present invention; however, especially beneficial results are obtained when 0.25 to 10 percent (based on the base stock) Ultraphos 11 (or less preferred, Ultraphos 12) used as one of the additives. Ultraphos 11 is marketed by Witco Chemical Company and has the following typical properties:

| | |
|---|---|
| $KV_{210}$ = 23.44 cs. | ASTM-VI = 142 |
| $KV_{100}$ = 217.20 cs. | VTF-VI = 132 |
| Melting Point = 0° C. | Glass Transition Temperature = −62° C. |

Elemental Analysis:
| | |
|---|---|
| Carbon | 58.16 percent |
| Hydrogen | 10.47 percent |
| Oxygen | 20.44 percent |
| Ash | 1.58 percent |
| Phosphorus | 5.77 percent |
| Sulfur | 0.4 percent (Schoniger) |
| Nitrogen | 0.10 percent |
| Chlorine | 10 ppm |

Alternatively, Antara LB400 (General Aniline and Film) can be used instead of Ultraphos as a low static modifier.

Another useful, multipurpose additive package which is useful in such lubricants is 2 to 15 percent Anglamol 93, which has been previously described and which is a product of Lubrizol Company and comprises a mixture of zinc phosphorodithioate and chlorinated hydrocarbons, a typical analysis being 3 percent zinc, 3 percent phosphorus, 16.5 percent chlorine and 16.0 percent sulfur.

The blended fluids and limited slip differential lubricants referred to herein, especially that of Example 4, can be used to increase traction between two rolling elements. When traction fluid is used to lubricate high speed ball bearings—for an example, the main shaft bearings in a turbine engine—it reduces ball skidding. Ball skidding is one of the factors limiting shaft speed. Accordingly, such lubricants can be used for high speed and highly loaded bearings. They can also be used for lubrication of overrunning clutches.

During engagement, there is a sliding motion between the cam or rollers and the races in overrunning clutches. Since wear occurs during the engagement period, a lubricant which reduces engagement time will reduce wear and extend service life. In one test, engagement was reduced from 11 to 2 revolutions simply by replacing the conventional petroleum oil grease with a grease component of a naphthene-paraffin blend similar to that of Example 4. The traction fluid and its grease show the greatest advantage in clutches where load is high enough to elastically deform the rollers and cams.

Example 6

Friction data was obtained for a number of oils. The friction data was used to plot the curves in FIGS. 2, 3 and 4 hereof. The data for FIGS. 2 and 4 were obtained by the LVFA method (using the apparatus marketed by Roxana Machine Works, St. Louis, Mo). The data for FIG. 3 was obtained by the R-H friction method, using the General Motors Corporation apparatus.

The following table identifies the oils of FIGS. 2, 3 and 4:

| Oil No. | |
|---|---|
| 1 | The blended hydrocarbon portion of Oil 4 |
| 2 | Oil 1 plus one volume percent Ultraphos 11 |
| 3 | Oil 1 plus additives* |
| 4** | Oil 3 plus one volume percent Ultraphos 11 |
| 5 | Commercial Petroleum base LSD fluid (Texaco TL3450) |
| 6 | Hydrogenated true polyisobutylene |
| 7 | Oil 6 plus one volume percent Ultraphos 11 |
| 8 | Oil 6 plus five volume percent Ultraphos 11 |

*The additives are those of the lubricant of Example 5, excepting the Ultraphos 11.
**Oil 4 is the lubricant of Example 5.

The invention claimed is:

1. In the process of lubricating a controlled-slip differential with a lubricating composition, the improvement wherein the lubricating composition comprises major amounts of a hydrocarbon base stock and friction improving amounts of synthetic sulfurized oil consisting essentially of a co-sulfurized blend of a triglyceride and an acyclic $C_2$–$C_{128}$ monoolefin.

2. Process of claim 1 wherein the base stock has a kinematic viscosity in the range of 1.5 to 200.0 cs. and said acyclic monoolefin contains in the range of 12 to 24 carbon atoms.

3. Process of claim 2 wherein said base stock consists essentially of a paraffinic petroleum oil having a viscosity-gravity constant no greater than 0.819.

4. Process of claim 1 wherein said base stock consists essentially of a blend of at least one $C_{13}$–$C_{29}$ naphthene and from 0.1 to 20 parts by weight, based on said naphthene of at least one member from at least one of the following groups (a), (b), (c) and (d):
   (a) a synthetic liquid $C_3$–$C_8$ olefin homopolymer, copolymer or terpolymer;
   (b) a member from group (a) above which is at least partially hydrogenated;
   (c) a severely hydrorefined naphthenic mineral oil lube containing less than one percent of gel aromatic hydrocarbons; and
   (d) a severely hydrorefined paraffinic mineral oil lube containing less than one percent of gel aromatic hydrocarbons.

5. Process of claim 2 wherein the fatty-acid moieties of said triglyceride consist essentially of 9 to 22 carbon atoms and at least 45 mole percent of said moieties contain an ethylenically unsaturated carbon-to-carbon double bond.

* * * * *